United States Patent
Yamada

(10) Patent No.: US 9,646,566 B2
(45) Date of Patent: May 9, 2017

(54) MEDICAL IMAGE DISPLAY CONTROL APPARATUS AND OPERATION METHOD OF THE SAME, AND MEDIUM

(71) Applicant: FUJIFILM Corporation, Tokyo (JP)

(72) Inventor: Kenta Yamada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 24 days.

(21) Appl. No.: 14/619,397

(22) Filed: Feb. 11, 2015

(65) Prior Publication Data

US 2015/0235613 A1     Aug. 20, 2015

(30) Foreign Application Priority Data

Feb. 14, 2014 (JP) ................................ 2014-026294

(51) Int. Cl.
*G09G 5/02* (2006.01)
*G06T 3/40* (2006.01)

(52) U.S. Cl.
CPC ............ *G09G 5/02* (2013.01); *G06T 3/4007* (2013.01); *G06T 2207/10004* (2013.01); *G06T 2207/10081* (2013.01); *G06T 2207/10088* (2013.01); *G06T 2207/30048* (2013.01); *G06T 2207/30061* (2013.01)

(58) Field of Classification Search
None
See application file for complete search history.

(56) References Cited

U.S. PATENT DOCUMENTS

| | | | |
|---|---|---|---|
| 6,981,011 B1 * | 12/2005 | Napolitano | G06F 1/03 708/270 |
| 2011/0313291 A1 * | 12/2011 | Chono | A61B 8/08 600/440 |

(Continued)

FOREIGN PATENT DOCUMENTS

| | | | |
|---|---|---|---|
| JP | 2012-105969 A | 6/2012 |
| JP | 2013-040829 A | 2/2013 |

OTHER PUBLICATIONS

Communication dated Jul. 2, 2015 from the European Patent Office in counterpart application No. 15154549.8.

*Primary Examiner* — Kee M Tung
*Assistant Examiner* — Yanna Wu
(74) *Attorney, Agent, or Firm* — Sughrue Mion, PLLC

(57) ABSTRACT

Providing a parameter calculation unit that calculates parameters representing medical functional information for pixel positions of the medical image, wherein the upper and lower limit values of the parameter medically represent the same functional information and whose value changes cyclically between these values, an interpolation parameter calculation unit that obtains, for a pixel position for which the parameter is not calculated, a parameter by interpolation, the unit calculating a parameter obtained by the interpolation using a cyclic function in which the interpolation direction differs according to the difference between the parameters calculated for two pixel positions, a display color group storage unit that includes a color group in which the same color corresponds to the upper and lower limit values of the parameter and whose color changes with the magnitude of the parameter, and a mapping unit that maps the parameters based on the color group.

10 Claims, 7 Drawing Sheets

(56) References Cited

U.S. PATENT DOCUMENTS

2012/0263368 A1* 10/2012 Nakano ................ A61B 6/032
                                                    382/133
2012/0300904 A1* 11/2012 Shimada .............. A61B 6/4291
                                                    378/62
2012/0310074 A1   12/2012 Yamamori et al.

* cited by examiner

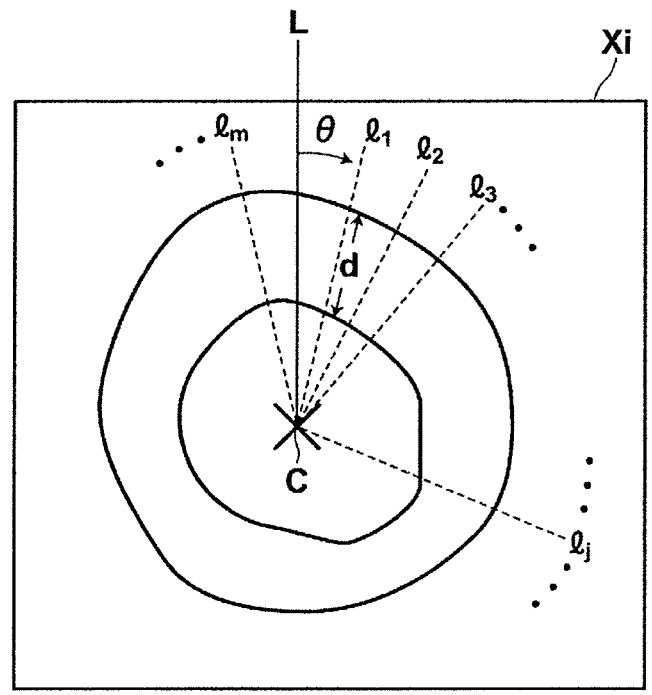
FIG.4
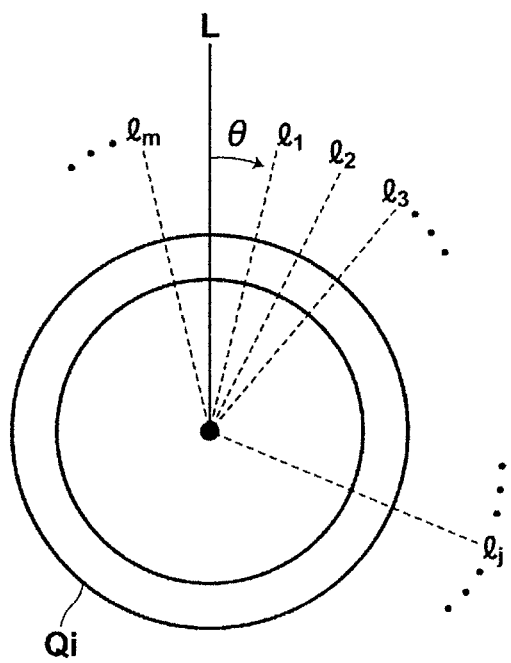

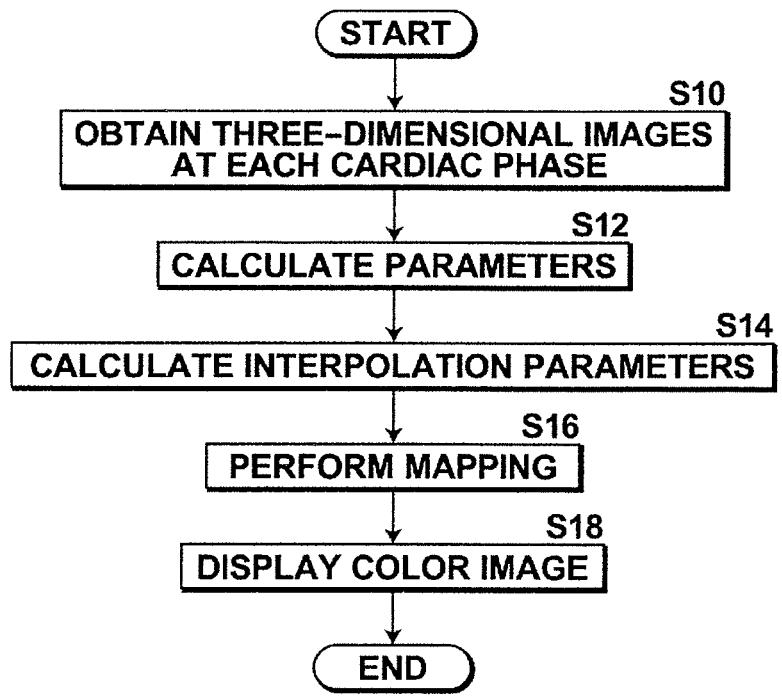
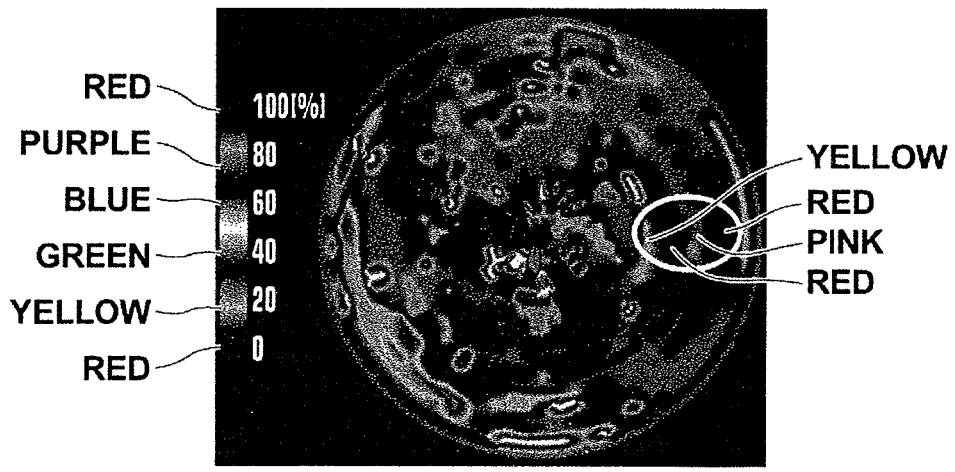

MEDICAL IMAGE DISPLAY CONTROL APPARATUS AND OPERATION METHOD OF THE SAME, AND MEDIUM

CROSS-REFERENCE TO RELATED APPLICATIONS

The present application claims priority under 35 U.S.C. §119 to Japanese Patent Application No. 2014-026294 filed on Feb. 14, 2014, the content of which is hereby expressly incorporated herein by reference in its entirety.

BACKGROUND OF THE INVENTION

Field of the Invention

The present invention relates to a medical image display control apparatus that displays a color image in which a parameter representing medical functional information is mapped and an operation method of the same, and a medical image display control program.

Description of the Related Art

Heretofore, a bull's eye display method has been used as a method for displaying cardiac functional information (as described, for example, in Japanese Unexamined Patent Publication No. 2012-105969). The bull's eye display method is a method that, when a heart is approximated by an ellipsoidal model and considered, displays images representing functional evaluations of cardiac information on slice surfaces cut at a regular interval in a direction traversing the major axis of the ellipsoid by concentrically arranging the images. In the bull's eye method, the functional information of a slice surface near one of the major vertices of the ellipsoid model is dispose near the center of the concentric circles and functional information of a slice surface near the other of the major vertices of the ellipsoid mode is disposed outer side of the concentric circles.

For the functional information described above, for example, analysis results of three-dimensional medical images captured by a CT (Computed Tomography) system and a MRI (Magnetic Resonance Imaging) system, and imaged results of myocardial scintigraphy (SPECT) are used. For example, Japanese Unexamined Patent Publication No. 2013-040829 proposes that, based on three-dimensional medical images of a plurality of phases obtained by electrocardiogram-gated SPECT, a maximally shifted phase is obtained for each pixel and the maximally shifted phase is displayed by allocating a color.

SUMMARY OF THE INVENTION

Here, when a color image is displayed by allocating a color to functional information, if, for example, a parameter representing the functional information is a parameter whose upper limit value and lower limit value represent medically the same functional information and whose value changes cyclically between the upper limit value and the lower limit value, and if different colors are allocated to the upper limit value and the lower limit value, parameters are displayed in different colors even though the same functional information are represented. Therefore, even when parameters representing the same functional information are adjacently distributed, they are displayed in rapid color change, so that the observer cannot instantaneously recognize that the same functional information is adjacently distributed, whereby diagnostic efficiency is degraded.

More specifically, if the parameter representing functional information is, for example, a cardiac phase R-R value where the cardiac ventricular wall thickness becomes maximum or minimum, the cardiac phase R-R value represents cardiac diastole-contraction state within a single beat by 0 to 100%. Here, the upper limit value 100% and the lower limit value 0% represent the same contraction state, so that these values are the parameters representing the same functional information. If different colors are allocated to the upper limit value and the lower limit value as described above, however, they are displayed in different colors even though they are the parameters representing the same functional information.

FIG. 12 shows an example bull's eye image displayed with the use of a color group in which pink is allocated to the upper limit value 100% and blue is allocated to the lower limit value 0%. The ellipsoidal area shown in FIG. 12 is an area in which values of cardiac phases near the upper limit value 100% and values of cardiac phases near the lower limit value 0% are adjacently distributed, but rapid color changes from blue and green to pink appear, so that it cannot be instantaneously recognized that similar functional information is distributed.

Therefore, in order to avoid such rapid color changes as described above, it is conceivable that bull's eye display is implemented with the use of a color group in which the same red is allocated to the upper limit value 100% and the lower limit value 0%, as shown in FIG. 13.

But, when parameters representing functional information are mapped and displayed as described above, it is generally practiced that parameters are calculated for only some of the pixel positions, instead of all of the pixel positions, from the viewpoint of calculation efficiency, and with respect to a pixel position for which the parameter is not calculated, a parameter is calculated by interpolation.

When calculating a parameter by interpolation as described above, simple interpolation with the use of two adjacent parameter values yields a value near the median value if, for example, the two parameters are values near the upper limit value and the lower limit value. Therefore, even if the color group shown in FIG. 13 is used, the color corresponding to the parameter calculated by the interpolation is blue to green, resulting in a rapid color change after all. That is, as the area shown by the ellipsoid in FIG. 13, a green or a blue portion is disposed between red and pink regions and the observer cannot instantaneously recognize that similar functional information is adjacently distributed.

Japanese Unexamined Patent Publication No. 2012-105969 and Japanese Unexamined Patent Publication No. 2013-040829 describe no method of solving the problem that occurs when a recursive parameter like that described above is displayed as a color image.

In view of the circumstances described above, it is an object of the present invention to provide a medical image display control apparatus capable of displaying, when a color image is displayed by mapping a parameter whose upper limit value and the lower limit value medically represent the same functional information and whose value changes cyclically between the upper limit value and the lower limit value, parameters representing the same functional information in the same color and smoothing a color change between a parameter calculated by interpolation and a parameter used for the interpolation, thereby improving diagnostic efficiency of an observer, and an operation method of the same. It is a further object of the present invention to provide a medical image display control program.

A medical image display control apparatus of the present invention includes a parameter calculation unit that calculates, using a medical image, parameters representing medical functional information for at least two pixel positions of the medical image, wherein the upper limit value and the lower limit value of the parameter medically represent the same functional information and whose value changes cyclically between the upper limit value and the lower limit value, an interpolation parameter calculation unit that obtains, with respect to a pixel position for which the parameter is not calculated, a parameter from the parameters calculated for the at least two pixel positions by interpolation, the unit calculating a parameter obtained by the interpolation using a cyclic function in which the interpolation direction differs according to the difference between the parameters calculated for the at least two pixel positions, a display color group storage unit that includes a color group in which the same color corresponds to the upper limit value and the lower limit value of the parameter and whose color changes with the magnitude of the parameter, a mapping unit that performs mapping of the parameters based on the color group, and a display control unit that displays the mapped color image.

In the medical image display control apparatus of the present invention, information representing a cardiac phase may be used as the parameter.

Further, information representing a pulmonary respiratory phase may be used as the parameter.

Still further, phase information representing a blood vessel flow velocity may be used as the parameter.

Further, a CT image or a MR image of a heart, a lung, or a head may be used as the medical image.

Still further, the mapping unit may perform mapping into a two-dimensional sectional medical image, a three-dimensional medical image, or a bull's eye image.

Further, the color group may include a plurality of colors of different hues.

Still further, a cyclic function represented by the formula given below may be used as the cyclic function:

$$x = \begin{cases} f(x) = f(x+R) \\ R = s_{max} - s_{min} \\ ts_1 + (1-t)s_2 & s_1 - s_2 \leq \dfrac{s_{max} - s_{min}}{2} \\ t(s_1 - R) + (1-t)s_2 & s_1 - s_2 > \dfrac{s_{max} - s_{min}}{2} \end{cases}$$

where: f(x) is the value representing a color corresponding to a parameter x; $S_1$ and $S_2$ are parameters used for the interpolation in which $S_1 > S_2$; $S_{max}$ is the upper limit value of the parameter; $S_{min}$ is the lower limit value of the parameter; and t and 1-t represent the ratio between the distance from the pixel position of the parameter $S_2$ used for the interpolation to the pixel position of the parameter x obtained by the interpolation and the distance from the pixel position of the parameter $S_1$ used for the interpolation to the pixel position of the parameter x obtained by the interpolation.

An operation method of a medical image display control apparatus of the present invention is an operation method of a medical image display control apparatus which includes a parameter calculation unit, an interpolation parameter calculation unit, a mapping unit, and a display control unit, in which the parameter calculation unit calculates, using a medical image, parameters representing medical functional information for at least two pixel positions of the medical image, wherein the upper limit value and the lower limit value of the parameter medically represent the same functional information and whose value changes cyclically between the upper limit value and the lower limit value, the interpolation parameter calculation unit obtains, with respect to a pixel position for which the parameter is not calculated, a parameter from the parameters calculated for the at least two pixel positions by interpolation, the unit calculating a parameter obtained by the interpolation using a cyclic function in which the interpolation direction differs according to the difference between the parameters calculated for the at least two pixel positions, the mapping unit performs mapping of the parameters calculated for the at least two pixel positions and the parameter calculated by the interpolation based on a color group in which the same color corresponds to the upper limit value and the lower limit value of the parameter and whose color changes with the magnitude of the parameter, and the display control unit displays the mapped color image.

A medical image display control program of the present invention causes a computer to function as a parameter calculation unit that calculates, using a medical image, parameters representing medical functional information for at least two pixel positions of the medical image, wherein the upper limit value and the lower limit value of the parameter medically represent the same functional information and whose value changes cyclically between the upper limit value and the lower limit value, an interpolation parameter calculation unit that obtains, with respect to a pixel position for which the parameter is not calculated, a parameter from the parameters calculated for the at least two pixel positions by interpolation, the unit calculating a parameter obtained by the interpolation using a cyclic function in which the interpolation direction differs according to the difference between the parameters calculated for the at least two pixel positions, a display color group storage unit that includes a color group in which the same color corresponds to the upper limit value and the lower limit value of the parameter and whose color changes with the magnitude of the parameter, a mapping unit that performs mapping of the parameters based on the color group, and a display control unit that displays the mapped color image.

According to the medical image display control apparatus and the operation method of the same, and the medical image display control program of the present invention, when a mapped color image is displayed by allocating a color to a parameter representing medical functional information whose upper limit value and the lower limit value medically represent the same functional information and whose value changes cyclically between the upper limit value and the lower limit value is used, so that the upper limit value and the lower limit value may be displayed in the same color.

Further, when obtaining, with respect to a pixel position for which the parameter is not calculated, a parameter from the parameters calculated for at least two pixel positions by interpolation, a parameter obtained by the interpolation is calculated using a cyclic function in which the interpolation direction differs according to the difference between the parameters calculated for the at least two pixel positions, so that the color change between the interpolation parameter calculated by the interpolation and the parameter used for the interpolation may be smoothed, whereby diagnostic efficiency of the observer may be improved.

BRIEF DESCRIPTION OF THE DRAWINGS

FIG. 4 is a drawing for explaining a method of calculating the myocardial wall thickness.

FIG. 9 is a flowchart for explaining the operation of the medical image display system that uses one embodiment of the medical image display control apparatus of the present invention.

FIG. 10 shows an example bull's eye image displayed by the medical image display system that uses one embodiment of the medical image display control apparatus of the present invention.

DESCRIPTION OF THE PREFERRED EMBODIMENTS

Figure 1:
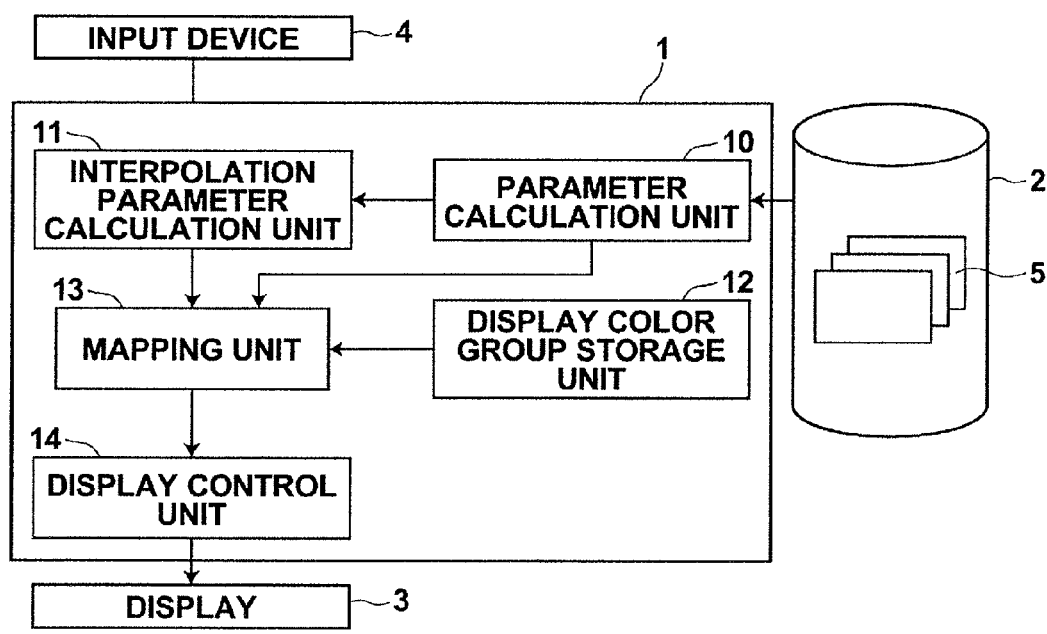
FIG. 1 is a block diagram of a medical image display system that uses one embodiment of the medical image display control apparatus of the present invention, schematically illustrating the configuration thereof.

An embodiment of the medical image display control apparatus, method, and program of the present invention will be described with reference to the accompanying drawings. FIG. 1 is a drawing schematically illustrating the configuration of a medical image display system that uses one embodiment of the medical image display control apparatus of the present invention.

As illustrated in FIG. 1, the medical image display system of the present embodiment includes a medical image display control apparatus 1, a storage device 2, a display 3, and an input device 4.

The medical image display control apparatus 1 is formed of one computer on which one embodiment of the medical image display control program is installed. The computer may be a workstation directly operated by a doctor that performs image diagnosis, a personal computer, or a server computer connected to these via a network. The medical image display control program is recorded on a recording medium, such as DVDs, CD-ROMs, or the like, or a server computer connected to a network and accessible from outside, and read out from the foregoing recording medium or the server computer in response to a request from a doctor, downloaded to the computer and installed. Further, the medical image display control program provided by SaaS (Software as a Service) via a network may also be used.

The medical image display control apparatus 1 of the present embodiment includes a central processing unit (CPU) and storage devices, such as a semiconductor memory, a hard disk in which the foregoing medical image display control program is installed, a SSD (Solid State Drive), and the like. By theses hardware devices, a parameter calculation unit 10, an interpolation parameter calculation unit 11, a display color group storage unit 12, a mapping unit 13, and a display control unit 14 are formed, as shown in FIG. 1. Then, each unit described above functions when the medical image display control program is executed by the central processing unit.

The parameter calculation unit 10 calculates so-called functional information representing a function of a subject based on a three-dimensional medical image obtained by imaging the subject with a CT (Computed Tomography) system, a MRI (Magnetic Resonance Imaging) system, or the like. The parameter calculation unit 10 of the present embodiment, in particular, calculates a parameter that represents medical functional information, in which the upper limit value and the lower limit value of the parameter medically represent the same functional information and whose value changes cyclically between the upper limit value and the lower limit value.

The medical functional information is information representing a function of a subject as described above and, for example, refers to information representing a function of an organ, such as heart, lung, brain, blood vessel, and the like, which may include, for example, information of a cardiac function, information of a pulmonary respiratory function, information representing a blood flow function of a blood vessel in a brain or an abdomen. Further, the term "medically represent the same functional information" refers to that the functional information of the foregoing organs can be deemed the same from the medical standpoint.

The foregoing "parameter whose upper limit value and lower limit value medically represent the same functional information and whose value changes cyclically between the upper limit value and the lower limit value" refers to a parameter whose upper limit value and lower limit value themselves are different but they represent the same functional information, as described above. Such a parameter may include, for example, a cardiac phase R-R value where cardiac ventricular wall thickness becomes maximum or minimum. The upper limit value of the cardiac phase R-R values is 100% and the lower limit value is 0% and the values themselves are different but a cardiac phase R-R value of 100% and a cardiac phase value of 0% represent the same cardiac contraction state, as described above, so that these values indicate the same functional information.

Further, such a parameter as described above may include, with respect to lungs, a pulmonary phase value where bronchus wall thickness or bronchus diameter becomes maximum or minimum. The upper limit value of the pulmonary phase values is 100% and the lower limit value is 0% as in the cardiac phase R-R values. Then, a pulmonary phase value of 100% and a pulmonary phase value of 0% represent the same pulmonary respiration state, so that these values indicate the same functional information. In a case where the pulmonary phase values are used, a three-dimensional medical image obtained by a CT system or a MRI system is used.

Still further, such a parameter as described above may include phase information values representing blood flow velocities of a blood vessel of a brain or an abdomen measured by phase-contrast method. The phase-contrast method is known as a method of measuring a blood flow velocity using a three-dimensional medical image obtained by a MRI system. The phase-contrast method is a method for generating a phase image by making use of a phase shift of a MR signal generated by the blood flow, in which the phase shift varies from 0 to $2\pi$. Then, a phase shift of 0 and a phase shift of 2π indicate the same blood flow velocity, so that these values indicate the same functional information.

Here, a detailed description will be made for calculating a cardiac phase where a ventricular wall thickness becomes maximum or minimum as a parameter based on a three-dimensional medical image. Note that the foregoing pulmonary phase value and the phase shift representing the blood flow velocity may be calculated by the various types of known methods.

Hereinafter, the foregoing cardiac phase parameter calculation method will be described in detail.

First, the parameter calculation unit 10 obtains 10 to 20 three-dimensional medical images of a heart in one cardiac cycle obtained by electrocardiogram-gated imaging with the use of a MSCT system or a DSCT system.

Figure 2:
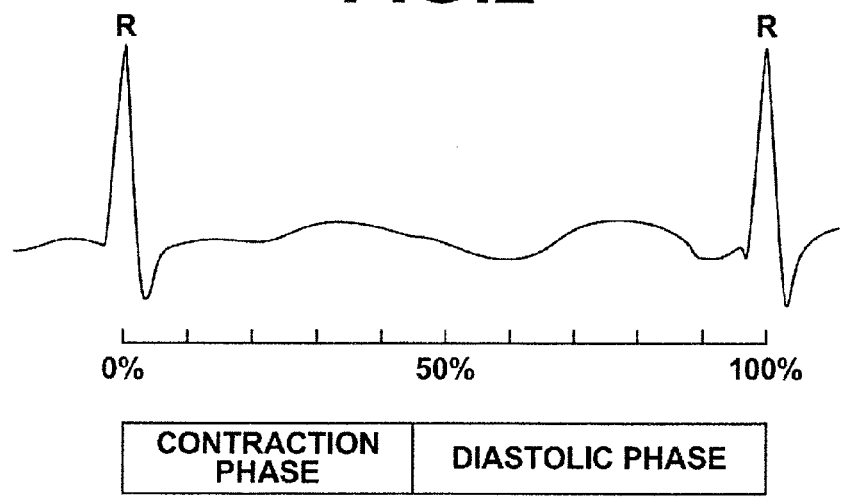
FIG. 2 is a drawing for explaining electrocardiogram-gated imaging.

The electrocardiogram-gated imaging will be described with reference to FIG. 2. The upper side of the drawing shows an electrocardiogram waveform. In electrocardiograms, the period from one R-wave to the next R-wave corresponds to one cardiac cycle. A cardiac phase (phase) is a position on the horizontal axis of the electrocardiogram and expressed in percentage with one cardiac cycle being taken as 100%. For example, if 10 three-dimensional medical images are obtained at an equal interval in one cardiac cycle, the phases where the three-dimensional medical images are obtained are represented as R-R0%, R-R10%, R-R20%, R-R30%, . . . , and R-R90%. Note that, although the cardiac beating varies between individuals, R-R0% to near R-R45% is a contraction phase and near R-R45% to R-R100% is a diastolic phase in most cases. Then, the R-R0% and the R-R100% are in the same cardiac diastolic-contraction state.

Then, the parameter calculation unit 10 calculates myocardial wall thicknesses from three-dimensional medical images of the heart at each cardiac phase.

Figure 3:
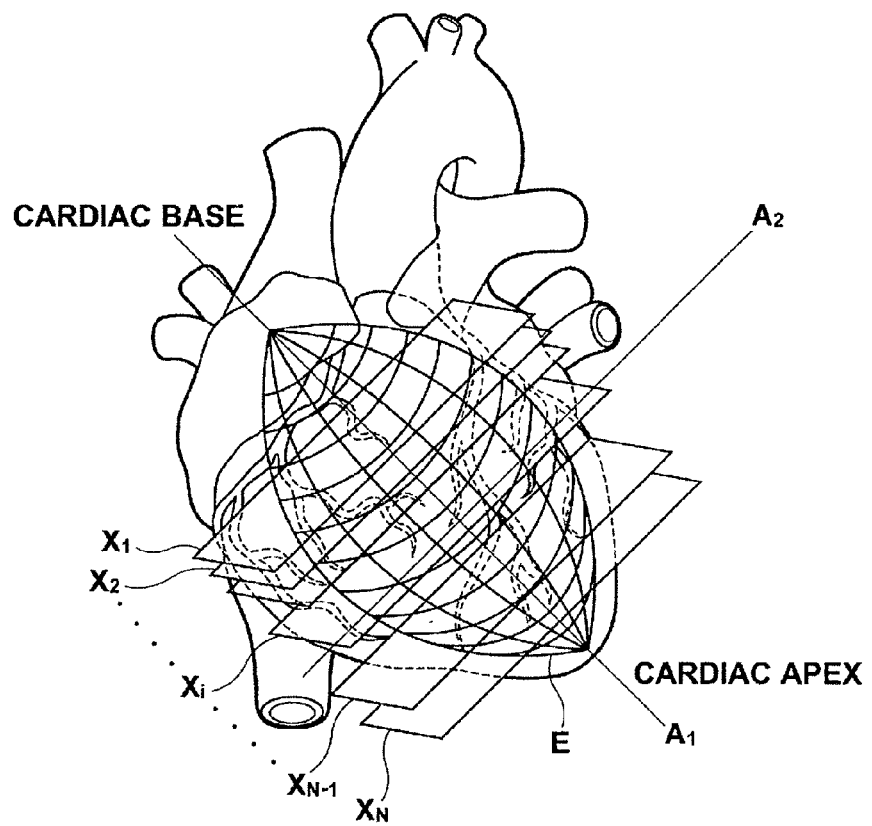
FIG. 3 is a drawing for explaining the relationship between a heart and a slice surface.

More specifically, a surface model of the heart is approximated by an ellipsoidal shape E, as shown in FIG. 3, based on the three-dimensional medical image representing the heart, and a long axis $A_1$ and a short axis $A_2$ of the heart are determined. The long axis $A_1$ is determined so as to extend from the cardiac base to the cardiac apex of the heart and to pass through the center of the ventricular region. The short axis $A_2$ is orthogonal to the long axis $A_1$.

A myocardial wall thickness is obtained by generating cross-sectional images of slice surfaces $X_1$, $X_2$, . . . , $X_i$, . . . , $X_{N-1}$, and $X_N$ obtained by cutting the heart in a direction traversing the long axis $A_1$, i.e. a direction of the short axis $A_2$, from the three-dimensional medical image. For example, an endocardium contour and an epicardium contour are extracted from the cross-sectional image of a slice surface $X_i$ as shown in FIG. 4, and a distance between the endocardium contour and the epicardium contour on each of lines $l_1$, $l_2$, $l_3$, . . . , $l_j$ . . . , and $l_m$ radially extending from a point C in the ventricular region through which the long axis passes on each slice surface $X_i$ is obtained as a wall thickness d.

Then, the parameter calculation unit 10 compares the wall thicknesses of the three-dimensional medical images at each cardiac phase and calculates a cardiac phase R-R value where the wall thickness becomes maximum or minimum with respect to a given pixel position. In this way, cardiac phases (R-R) where the wall thickness becomes maximum or minimum are calculated for at least two of some of pixel positions. Note that, in the present embodiment, some of pixel positions described above are assumed to be preset so as to be distributed uniformly at a regular interval on the surface of the ventricular region.

The interpolation parameter calculation unit 11 calculates a parameter of a pixel position for which the parameter is not calculated in the parameter calculation unit 10 by interpolation using the parameters calculated in the parameter calculation unit 10. Hereinafter, a parameter calculated by the interpolation is referred to as an interpolation parameter.

Figure 5:
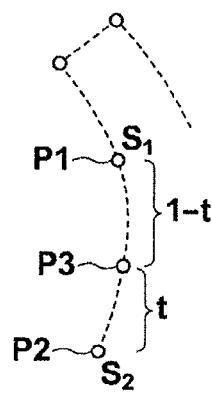
FIG. 5 is a drawing for explaining a parameter interpolation method.

For example, if the pixel positions for which parameters are calculated by the parameter calculation unit 10 are P1 and P2 shown in FIG. 5, and the parameter of P1 is $S_1$ and the parameter of P2 is $S_2$, the interpolation parameter calculation unit 11 calculates the interpolation parameter of pixel position P3 according to the ratio between the distance from P3 to P2 and the distance from P3 to P1, t:1-t. The interpolation parameter calculation unit 11, in particular, calculates an interpolation parameter using a cyclic function in which the interpolation direction differs according to the difference between the parameter $S_1$ of P1 and the parameter $S_2$ of P2. More specifically, the cyclic function used in the present embodiment is represented by a formula given below.

$$\text{Color} = f(x)$$
$$f(x) = f(x+R)$$
$$R = s_{max} - s_{min}$$

$$x = \begin{cases} ts_1 + (1-t)s_2 & s_1 - s_2 \leq \dfrac{s_{max} - s_{min}}{2} \quad (1) \\ t(s_1 - R) + (1-t)s_2 & s_1 - s_2 > \dfrac{s_{max} - s_{min}}{2} \quad (2) \end{cases}$$

where: f(x) in the foregoing formula is the cyclic function and is the value representing a color corresponding to a parameter or an interpolation parameter x; $S_1$ and $S_2$ are adjacent parameters used for the interpolation in which $S_1 > S_2$; $S_{max}$ is the upper limit value of the parameter; $S_{min}$ is the lower limit value of the parameter; and t and (1-t) represent the ratio between the distance from the pixel position of the parameter $S_2$ to the pixel position of the interpolation parameter x and the distance from the pixel position of the parameter $S_1$ to the pixel position of the interpolation parameter x.

As shown in the formula (1) above, if ($S_1$-$S_2$) is less than or equal to ($S_{max}$-$S_{min}$)/2, i.e., less than or equal to 50, the interpolation parameter calculation unit 11 calculates the interpolation parameter x by the equation shown in the foregoing formula (1). If the interpolation direction of the interpolation is described using an imaginary view, the interpolation direction is like the arrow shown in the left of FIG. 6. That is, the interpolation parameter x of the pixel position P3 is interpolated in the interpolation direction drawing closer to $S_1$ or $S_2$ according to the magnitudes of the t and 1-t with the intermediate value of the parameter $S_1$ and the parameter $S_2$ as the reference. In other words, a value in the range between the parameter $S_1$ and the parameter $S_2$ in the same recursive cycle is calculated as the interpolation parameter.

Figure 6:
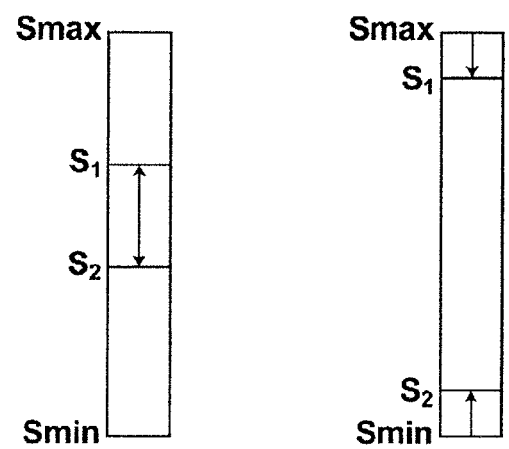
FIG. 6 is a drawing for explaining a method of calculating interpolation parameter using a cyclic function in which the interpolation direction differs according to a difference between the two parameters.

In the meantime, if ($S_1$-$S_2$) is greater than ($S_{max-Smin}$)/2, i.e., greater than 50, as shown in the formula (2) above, the interpolation parameter calculation unit 11 calculates the interpolation parameter x by the equation shown in the foregoing formula (2). In this case, $S_1$ is replaced with ($S_1$-R), as shown in the formula (2) above. As f(x) is a cyclic function, the replacement of $S_1$ with ($S_1$-R) indicates, in effect, that the interpolation parameter x of the pixel position P3 is interpolated in the interpolation direction drawing closer to $S_1$ or $S_2$ according to the magnitudes of t and 1-t with the upper limit value $S_{max}$ or the lower limit value $S_{min}$ as the reference, as shown in the right of FIG. 6. In other words, a value in the range between $S_{min}$ to $S_2$ or between $S_1$ to $S_{max}$ is calculated as the interpolation parameter.

As described above, the interpolation parameter calculation unit 11 calculates the interpolation parameter x by changing the interpolation direction according to the difference between the parameter $S_1$ of the pixel position P1 and the parameter $S_2$ of the pixel position P2 used in the interpolation. Such way of calculation for interpolation parameters allows a color change between parameters representing similar functional information to be smoothed, but details of the operation and effect will be described later.

Figure 7:
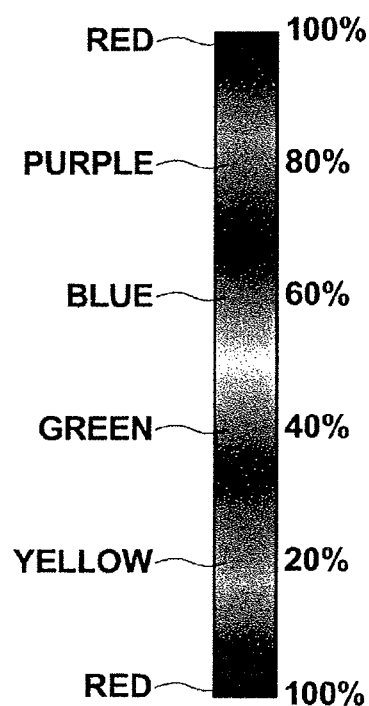
FIG. 7 illustrates an example color group associated with a parameter.
Figure 8:
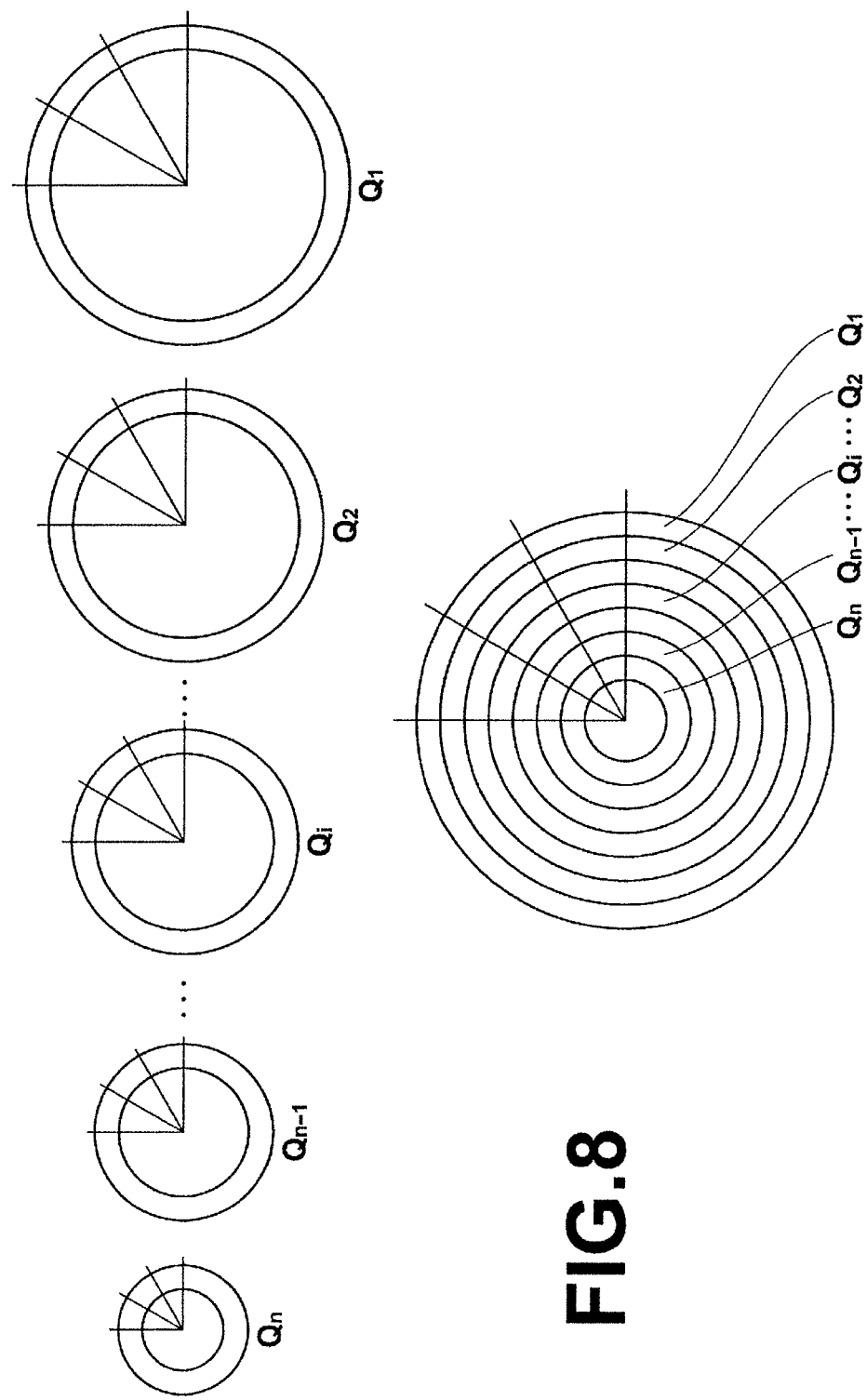
FIG. 8 is a drawing for explaining a method of generating a bull's eye image.

Next, the display color group storage unit 12 includes in advance a color group in which the same color represented by f(x) corresponds to the upper limit value and the lower limit value of the parameter and whose color changes with the magnitude of the parameter. More specifically, the color group of the present embodiment includes a plurality of colors which differ in hue according to the magnitude of f(x) corresponding to the parameter, and the color represented by f(x) corresponding to the upper limit value and the lower limit value of the parameter is red, and the colors change from red to yellow, from yellow to green, from green to blue, from blue to purple, and from purple to red toward the upper limit value from the lower limit value, as shown in FIG. 7.

The aforementioned "the same color" may be in a similarity level that causes colors to visually appear the same for the human, and there may be a color difference that cannot be distinguished by the human vision.

The mapping unit 13 generates a color image by performing mapping based on the parameters calculated by the parameter calculation unit 10, the interpolation parameters calculated by the interpolation parameter calculation unit 11, and the color group described above. The mapping unit 13 of the present embodiment generates a bull's eye image as the color image.

The bull's eye image is an image generated by changing the color according to the magnitudes of the parameters and the interpolation parameters calculated for pixel positions over the entire surface of the ventricular region, in which parameters and interpolation parameters of pixel positions on slice surfaces $X_1$, $X_2$, . . . near the cardiac base are displayed on concentric circles on the outer circumferential side remote from the center and parameters and interpolation parameters of pixel positions on slice surfaces $X_n$, $X_{n-1}$, . . . near the cardiac apex are displayed on concentric circles near the center.

Then, the bull's eye image is generated by arranging colors, on a concentric circle, corresponding to the parameters of pixel positions of each of the lines $l_1$, $l_2$, $l_3$, . . . , $l_j$, . . . , and $l_m$ on a slice according to the angle θ between a reference line L and each of the lines $l_1$, $l_2$, $l_3$, . . . , $l_j$, . . . , and $l_m$ and arranging colors corresponding to the interpolation parameters between the colors corresponding to the parameters, thereby generating a concentric circle $Q_i$, and superimposing concentric circles $Q_1$, $Q_2$, . . . , $Q_i$, . . . , $Q_{n-1}$, and $Q_n$.

The display control unit 14 displays the bull's eye image generated in the mapping unit 13 on the display 3.

The storage device 2 includes three-dimensional medical images 5 obtained by imaging subjects with a CT system, a MRI system, and the like.

The input device receives a given setting user input.

Next, an operation of the medical image display system of the present embodiment will be described with reference to the flowchart of FIG. 9.

First, three-dimensional medical images at each cardiac phase are read out from the storage device 2 and obtained by the parameter calculation unit 10 of the medical image display control apparatus 1 (S10). Based on the obtained three-dimensional medical images at each cardiac phase, the parameter calculation unit 10 calculates cardiac phases R-R where the wall thickness becomes maximum or minimum for some of pixel positions on the surface of the ventricular region as parameters (S12).

Then, the parameters calculated by the parameter calculation unit 10 are outputted to the interpolation parameter calculation unit 11, and the interpolation parameter calculation unit 11 calculates interpolation parameters by performing interpolation in the manner as described above using the inputted parameters (S14).

Values of f(x) corresponding to the parameters calculated in the parameter calculation unit 10 and interpolation parameters calculated in the interpolation parameter calculation unit 11 are outputted to the mapping unit 13. The mapping unit 13 obtains colors represented by the inputted f(x) which correspond to the parameters and interpolation parameters with reference to the color group stored in the display color storage unit 12, and generates a bull's eye image by mapping the obtained colors (S16).

The bull's eye image generated by the mapping unit 13 is outputted to the display control unit 14, and the display control unit 14 displays the inputted bull's eye image as a color image (S18). FIG. 10 shows an example bull's eye image generated and displayed in the manner as described above.

According to the medical image display system of the present embodiment, a color group in which the same color corresponds to the upper limit value and the lower limit value of the parameter and whose color changes with the magnitude of the parameter, so that the upper limit value and the lower limit value can be displayed in the same color.

Further, an interpolation parameter is calculated with the use of a cyclic function in which the interpolation direction differs according to the difference between the parameters used for the interpolation, so that the color change between the interpolation parameter and the parameter used for the interpolation may be smoothed, whereby diagnostic efficiency of the observer may be improved.

Figure 12:
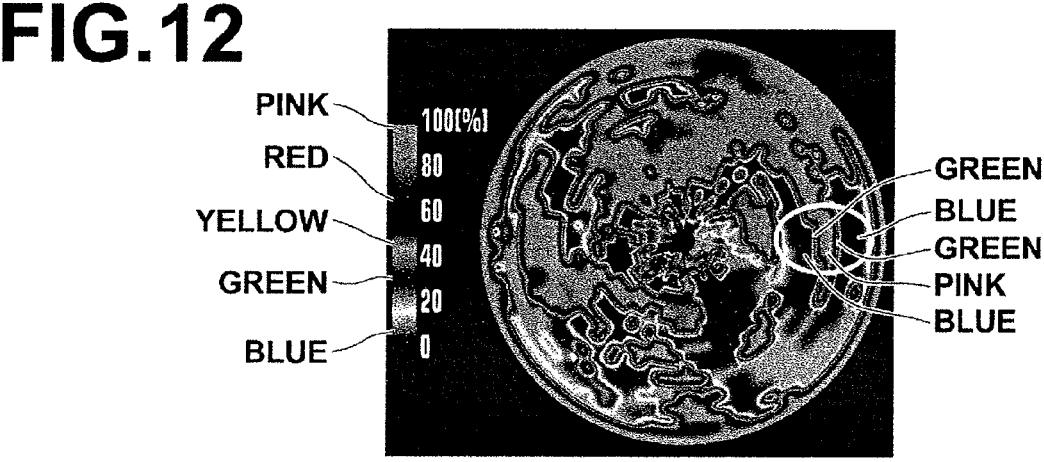
FIG. 12 shows an example bull's eye image generated with the use of a conventional color group.
Figure 13:
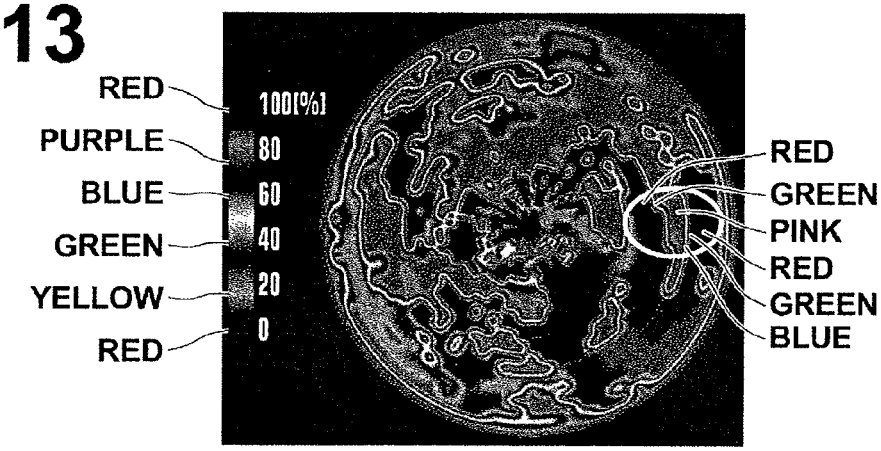
FIG. 13 show an example bull's eye image generated with the use of a color group in which the same color is allocated to the upper limit value and the lower limit value.

That is, in the example bull's eye images shown in FIGS. 12 and 13, rapid color changes appear in the ellipsoidal areas in which parameters representing similar functional information are distributed, but according to the bull's eye image displayed by the present embodiment and shown in FIG. 10, colors within the ellipsoidal area can be similar colors, such as red, yellow, pink, and the like, whereby color changes may be smoothed. This allows the observer to instantaneously recognize that the ellipsoidal area is an area in which parameters representing similar functional information are distributed, whereby diagnostic efficiency may be improved.

Figure 11:
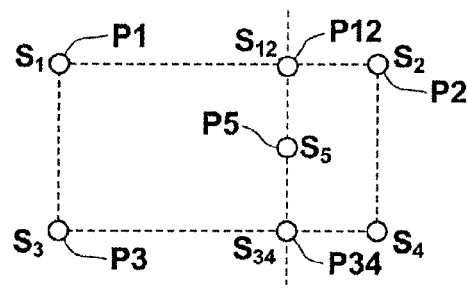
FIG. 11 is a drawing for explaining another example parameter interpolation method.

In the medical image display system of the foregoing embodiment, the interpolation parameter of the pixel position P3 between the two pixel positions P1 and P2 is calculated using the parameters $S_1$ and $S_2$ of the pixel positions P1 and P2. But, an arrangement may be adopted in which the interpolation parameter calculation method calculates, for example, an interpolation parameter of pixel position P4 surrounded by four pixel positions using parameters $S_1$, $S_2$, $S_3$, and $S_4$ of the four pixel positions, as shown in FIG. 11.

More specifically, an interpolation parameter $S_{12}$ of the pixel position P12 is calculated by interpolation using the parameter S₁ of the pixel position P1 and the parameter S₂ of the pixel position P2, and an interpolation parameter S₃₄ of the pixel position P34 is calculated by interpolation using the parameter S₃ of the pixel position P3 and the parameter S₄ of the pixel position P4, and the interpolation parameter S₅ of the pixel position P5 is calculated by interpolation using the interpolation parameter S₁₂ of the pixel position P12 and the interpolation parameter S₃₄ of the pixel position P34.

Further, an interpolation parameter S₁₃ may be calculated by interpolation using the parameter S₁ and the parameter S₃, and an interpolation parameter S₂₄ may be calculated by interpolation using the parameter S₂ and the parameter S₄, and an interpolation parameter S₅ of the pixel position P5 may be calculated by interpolation using the interpolation parameter S₁₃ and the interpolation parameter S₂₄. The foregoing way of calculation may yield the same result as that described above.

Further, in the medical image display system of the foregoing embodiment, a bull's eye image is generated by mapping colors corresponding to the parameters and the interpolation parameters described above, but color images generated by the mapping unit 13 are not limited to bull's eye images. For example, a color image may be generated by mapping colors corresponding to the parameters and the interpolation parameters into a two-dimensional tomographic image or a color image may be generated by mapping colors corresponding to the parameters and the interpolation parameters into a three-dimensional medical image.

What is claimed is:

1. A medical image display control apparatus, comprising:
   a memory which stores computer-executable instructions; and
   a processor which executes the stored instructions, which when executed by the processor cause the processor to:
   calculate, using a medical image, parameters representing medical functional information for at least two pixel positions of the medical image, wherein the upper limit value and the lower limit value of each of the parameters medically represent the same functional information and whose value changes cyclically between the upper limit value and the lower limit value;
   calculate, with respect to a pixel position for which the parameter is not calculated, an interpolated parameter from the parameters which are calculated for the at least two pixel positions by interpolation, the calculating of the interpolated parameter is obtained by using a cyclic function in which the interpolation direction differs according to the difference between the parameters calculated for the at least two pixel positions;
   control the memory to store a color group in which the same color corresponds to the upper limit value and the lower limit value of said each of the parameters and whose color changes with the magnitude of said each of the parameters;
   map the parameters which are calculated for the at least two pixel positions and the interpolated parameter to the color group and generate a mapped color image based on the mapping and the medical image; and
   controls a display to display the mapped color image, wherein the parameters calculated for the at least two pixel positions represent a function of a part of a body.

2. The medical image display control apparatus as claimed in claim 1, wherein the parameters represent a cardiac phase.

3. The medical image display control apparatus as claimed in claim 1, wherein the parameters represent a pulmonary respiratory phase.

4. The medical image display control apparatus as claimed in claim 1, wherein the parameters are phase information representing a blood vessel flow velocity.

5. The medical image display control apparatus as claimed in claim 1, wherein the medical image is a CT image or a MR image of a heart, a lung, or a head.

6. The medical image display control apparatus as claimed in claim 1, wherein the processor maps into a two-dimensional sectional medical image, a three-dimensional medical image, or a bull's eye image.

7. The medical image display control apparatus as claimed in claim 1, wherein the color group comprises a plurality of colors of different hues.

8. The medical image display control apparatus as claimed in claim 1, wherein the cyclic function is represented by a formula given below:

$$f(x) = f(x+R)$$
$$R = s_{max} - s_{min}$$
$$x = \begin{cases} ts_1 + (1-t)s_2 & s_1 - s_2 \leq \frac{s_{max} - s_{min}}{2} \\ t(s_1 - R) + (1-t)s_2 & s_1 - s_2 > \frac{s_{max} - s_{min}}{2} \end{cases}$$

where: f(x) is the value representing a color corresponding to a parameter x; S1 and S2 are parameters used for the interpolation in which S1>S2; Smax is the upper limit value of the parameter; Smin is the lower limit value of the parameter; and t and 1-t represent the ratio between the distance from the pixel position of the parameter S2 used for the interpolation to the pixel position of the parameter x obtained by the interpolation and the distance from the pixel position of the parameter S1 used for the interpolation to the pixel position of the parameter x obtained by the interpolation.

9. An operation method of a medical image display control apparatus which comprises a processor and a memory and which executes the method comprising:
   calculating, using a medical image, parameters representing medical functional information for at least two pixel positions of the medical image, wherein the upper limit value and the lower limit value of each of the parameters medically represent the same functional information and whose value changes cyclically between the upper limit value and the lower limit value;
   calculating, by an interpolation, with respect to a pixel position for which the parameter is not calculated, an interpolated parameter; the calculating of the interpolated parameter is obtained by using a cyclic function in which the interpolation direction differs according to the difference between the parameters which are calculated for the at least two pixel positions;
   mapping the parameters which are calculated for the at least two pixel positions and the interpolated parameter to a color group in which the same color corresponds to the upper limit value and the lower limit value of said each of the parameters and whose color changes with the magnitude of said each of the parameters;
   generating a mapped color image based on the mapping and the medical image; and controlling a display to display the mapped color image,
wherein the parameters calculated for the at least two pixel positions represent a function of a part of a body.

10. A non-transitory computer-readable recording medium containing a medical image display control program for causing a computer to:
  calculate, using a medical image, parameters representing medical functional information for at least two pixel positions of the medical image, wherein the upper limit value and the lower limit value of each of the parameters medically represent the same functional information and whose value changes cyclically between the upper limit value and the lower limit value;
  obtain, by interpolation, with respect to a pixel position for which the parameter is not calculated, an interpolated parameter from the parameters which are calculated for the at least two pixel positions;
  calculate the interpolated parameter by using a cyclic function in which the interpolation direction differs according to the difference between the parameters which are calculated for the at least two pixel positions;
  store a color group in which the same color corresponds to the upper limit value and the lower limit value of said each of the parameters and whose color changes with the magnitude of said each of the parameters;
  map the parameters which are calculated for the at least two pixel positions and the interpolated parameter to the color group;
  generate a mapped color image based on the mapping and the medical image; and
  display the mapped color image,
  wherein the parameters calculated for the at least two pixel positions represent a function of a part of a body.

* * * * *